(12) United States Patent
Hsiao (10) Patent No.: US 11,400,314 B2
(45) Date of Patent: Aug. 2, 2022

(54) PHOTON EMISSION DETECTION DEVICE AND NEUTRON CAPTURE THERAPY SYSTEM WITH THE SAME

(71) Applicant: NEUBORON MEDTECH LTD., Jiangsu (CN)

(72) Inventor: Ming-Chen Hsiao, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 391 days.

(21) Appl. No.: 16/553,380

(22) Filed: Aug. 28, 2019

(65) Prior Publication Data
US 2019/0388710 A1   Dec. 26, 2019

Related U.S. Application Data

(63) Continuation of application No. PCT/CN2017/092733, filed on Jul. 13, 2017.

(30) Foreign Application Priority Data

May 12, 2017   (CN) .......................... 20172052372.X
May 12, 2017   (CN) .......................... 201710332087.6

(51) Int. Cl.
   *A61N 5/10*      (2006.01)
   *A61B 6/00*      (2006.01)
   *H05H 3/06*      (2006.01)

(52) U.S. Cl.
   CPC .......... *A61N 5/1067* (2013.01); *A61B 6/4258* (2013.01); *A61N 5/1001* (2013.01);
   (Continued)

(58) Field of Classification Search
   CPC ...... A61N 2005/1052; A61N 2005/109; A61N 2005/1085–1098; A61N 5/10–1084; H05H 3/06
   See application file for complete search history.

(56) References Cited

U.S. PATENT DOCUMENTS

| 5,825,031 A | 10/1998 | Wong et al. |
| 2003/0226972 A1 | 12/2003 | Wong et al. |

(Continued)

FOREIGN PATENT DOCUMENTS

| CN | 1147967 A | 4/1997 |
| CN | 104136078 A | 11/2014 |

(Continued)

OTHER PUBLICATIONS

International Search Report of PCT/CN2017/092733, dated Feb. 13, 2018.

*Primary Examiner* — Thaddeus B Cox
(74) *Attorney, Agent, or Firm* — Locke Lord LLP; Tim Tingkang Xia, Esq.

(57) ABSTRACT

A boron neutron capture therapy system includes a neutron capture therapy device, a photon emission detection device and a treatment bed. The photon emission detection device includes a detecting portion surrounding the periphery of the treatment bed and detecting gamma rays generated after irradiating a boron-containing drug with neutrons; the detecting portion includes a first detecting portion and a second detecting portion moving away from or close to the first detecting portion so that the detecting portion forms a ring with the radius being increased or decreased; and the ring surrounds the treatment bed. The photon emission detection device for use in the boron neutron capture therapy system can change the radius of the ring, surrounding an irradiated object, of the detecting portion according to the actual condition in the boron neutron capture therapy so as to improve the detection precision of the photon emission detection device.

20 Claims, 3 Drawing Sheets

(52) U.S. Cl.
CPC ............. *A61N 5/1081* (2013.01); *H05H 3/06* (2013.01); *A61N 2005/109* (2013.01); *A61N 2005/1098* (2013.01)

(56) References Cited

U.S. PATENT DOCUMENTS

| | | | |
|---|---|---|---|
| 2006/0113482 A1* | 6/2006 | Pelizzari | A61N 5/1065 250/370.09 |
| 2008/0230704 A1 | 9/2008 | Daghighian | |
| 2008/0272284 A1* | 11/2008 | Rietzel | G01T 1/29 250/252.1 |
| 2010/0108896 A1 | 5/2010 | Surti et al. | |
| 2011/0024636 A1* | 2/2011 | Gagnon | G01T 1/2985 250/362 |
| 2011/0224534 A1* | 9/2011 | Yamaya | G01T 1/243 600/411 |
| 2012/0068076 A1* | 3/2012 | Daghighian | A61B 6/037 250/363.03 |
| 2012/0165651 A1* | 6/2012 | Yamaya | A61N 5/1049 600/411 |
| 2012/0253096 A1* | 10/2012 | Teshigawara | A61N 5/1039 600/1 |
| 2015/0087960 A1* | 3/2015 | Treffert | A61B 6/025 600/411 |
| 2015/0366519 A1* | 12/2015 | Furuta | A61B 6/037 600/431 |
| 2016/0158579 A1 | 6/2016 | LIU et al. | |
| 2020/0261043 A1* | 8/2020 | Majewski | A61B 6/502 |

FOREIGN PATENT DOCUMENTS

| | | |
|---|---|---|
| CN | 105445777 A | 3/2016 |
| CN | 105536153 A | 5/2016 |
| CN | 106264585 A | 1/2017 |
| CN | 104174121 B | 5/2017 |
| CN | 104919337 B | 1/2018 |
| CN | 106552322 B | 8/2018 |
| EP | 1860465 A2 | 11/2007 |
| JP | 2016214760 A | 12/2016 |
| WO | 2015124023 A1 | 8/2015 |

\* cited by examiner

PHOTON EMISSION DETECTION DEVICE AND NEUTRON CAPTURE THERAPY SYSTEM WITH THE SAME

CROSS-REFERENCE TO RELATED PATENT APPLICATION

This application is a continuation application of International Application No. PCT/CN2017/092733, filed on Jul. 13, 2017, which claims priority to Chinese Patent Application No. 201710332087.6, filed on May 12, 2017 and Chinese Patent Application No. 201720523721.X, filed on May 12, 2017, the disclosures of which are hereby incorporated by reference.

FIELD

The present invention relates to the field of medical devices, and more particularly to a photon emission detection device and a boron neutron capture therapy system with the same.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Photon emission computed tomography is an advanced device and imaging method for nuclear medicine. Photon emission computed tomography includes single photon emission computed tomography (named SPECT or single photon emission for short) and positron emission tomography (named PET or positron emission for short), label radioactive substances (such as $^{99m}$Tc, $^{123}$I, etc.) on radiopharmaceuticals (which may be a protein or organic molecule). The labeled drugs are generally selectively absorbed by different parts of the human body. The photon emission uses gamma rays emitted by a single-photon radionuclide (such as $^{99m}$Tc, $^{123}$I, etc.) injected into a human body to reconstruct an image with computer aid to form a tomographic image of the corresponding part of the body. For example, drugs that can accumulate in the myocardium are used for photon emission imaging of the heart. These organs, which absorb drugs labeled with a certain amount of radioactive material, will appear bright in the image, and if the organ has abnormal absorption, it will cause the organ to be abnormally bright or dark.

At present, almost all photon emission detection devices belong to the rotary gamma camera type, that is, a high-quality gamma camera probe fixed on a precision circular slide track is driven by a computer to rotate around the detected object to collect information, then data processing is performed by a computer to reconstruct a spatial image of the detected object, and the tomographic image of the object is displayed according to the body axis transverse, sagittal, coronal, or arbitrary cross-sectional directions. If it is considered to place a photon emission detection device in a BNCT (boron neutron capture therapy) room, by administering a boron ($^{10}$B)-containing drug to a patient and irradiating the boron ($^{10}$B)-containing drug with a neutron beam generated by the neutron capture therapy device, gamma rays are generated, and then the generated gamma rays are detected by the photon emission detection device. Because in the neutron ray environment, the number of moving parts must be small and rapid detection is required, while in the prior art, the rotation of the probe requires many moving parts to rotate the probe and the detection speed is slow, to overcome the problem, a full-ring photon emission detection device is often used in the market to reduce the number of moving parts by rotating the entire detection device to avoid rotating all the probes. However, there are several problems with this full-ring photon emission detection device, for example, the full-ring photon emission detection device is susceptible to the positioning device of the fixed body, the detecting radius is fixed, and cannot be adjusted according to the actual condition of the patient, thus a more accurate positioning cannot be obtained, resulting in failure to obtain more accurate information.

Therefore, it is necessary to improve the photon emission detection device of the prior art.

SUMMARY

In order to improve the detecting accuracy of the photon emission detection device, an aspect of the present disclosure provides a photon emission detection device, the photon emission detection device includes a treatment bed; and a detecting portion including a first detecting portion and a second detecting portion on two sides of the treatment bed respectively; wherein the first detecting portion and the second detecting portion move away from or close to each other so that the detecting portion forms a ring whose radius can be increased or decreased, and the ring surrounds the treatment bed. Adjusting the radius of the ring according to the actual situation of the detected object (such as the position and the size) so as to improve the detecting accuracy of the photon emission detection device.

Further, each of the first detecting portion and the second detecting portion is mounted with a probing device configured to rotate relative to the treatment bed, and the detecting portion detects gamma rays generated by a boron neutron capture reaction through the probing device. In certain embodiments, the rotating angles of the probing devices in the first detecting portion and/or the second detecting portion to the treatment bed is 180 degree, actually the angels can be any other degrees, such as 45 degree, 90 degree or 135 degree. Since the first detecting portion and/or second detecting portion can move both along and around the treatment bed in several degrees of freedom, the largest degree of the rotating angle can be more than 180 degree.

Further, the photon emission detection device further comprises a first supporting frame and a second supporting frame respectively disposed on the two sides of the treatment bed, the first supporting frame comprises a first pedestal capable of moving on the ground, a first telescopic arm connected to the first pedestal and configured to stretch and retract in a vertical direction, and a first extending arm located at one end of the first telescopic arm and connected to the first detection portion, the first detection portion is disposed at the first extending arm, the second supporting frame comprises a second pedestal capable of moving on the ground, a second telescopic arm connected to the second pedestal and configured to stretch and retract in the vertical direction, and a second extending arm at one end of the second telescopic arm and connected to the detection portion, the second detection portion is disposed at the second extending arm, wherein the first supporting frame moves away from or close to the treatment bed in response to moving of the first pedestal, and the second supporting frame moves away from or close to the treatment bed in response to moving of the second pedestal.

More particularly, when the first telescopic arm and the second telescopic arm have a same telescopic distance, and the first pedestal and the second pedestal move towards each other until the first detection portion and the second detection portion are in contact with each other, the first detection portion and the second detection portion form a maximum ring having a maximum radius surrounding the treatment bed; and when the first telescopic arm and the second telescopic arm have different telescopic distances, and the first pedestal and the second pedestal move towards each other, the first detection portion and the second detection portion form a reduced ring having a reduced radius surrounding the treatment bed.

Further, the first detection portion and/or the second detection portion rotate/rotates relative to the treatment bed.

Further, a first rotating member is disposed between the first telescopic arm and the first extending arm, and a second rotating member is provided between the second telescopic arm and the second extending arm, the first extending arm rotates about the first rotating member so that the first detection portion rotates relative to the treatment bed, and the second extending arm rotates about the second rotating member so that the second detection portion rotates relative to the treatment bed.

More particularly, a track is arranged on the ground at each side of the treatment bed, and the first and second pedestals are respectively mounted on the track.

The treatment bed moves back and forth in the ring formed by the detection portion.

In order to improve the detecting accuracy of the photon emission detection device, another aspect of the present disclosure provides a photon emission detection device, the photon emission detection device is used in a boron neutron capture therapy system comprising a treatment bed and a neutron capture therapy device, wherein the neutron capture therapy device comprises an accelerator configured to generate a charged particle beam; a neutron generator configured to generate a neutron beam after being irradiated by the charged particle beam; a beam shaping assembly configured to shape the neutron beam; and a collimator configured to converge the neutrons generated by the neutron generator; wherein the photon emission detection device comprises a detection portion surrounding the treatment bed configured to detect gamma rays generated after irradiating a boron ($^{10}$B)-containing drug with neutrons, the detection portion forms a ring whose radius is configured to be increased or decreased, and the ring surrounds the treatment bed.

Further, the detection portion comprises a first detection portion and a second detection portion respectively disposed on each side of the treatment bed, the first detection portion and the second detection portion moves away from or close to each other so that the ring radius of the detection portion is configured to be increased or decreased.

Further, each of the first detection portion and the second detection portion is mounted with a probing device configured to rotate relative to the treatment bed, and the detection portion detects the gamma rays by the probing device.

More particularly, the first detection portion and/or the second detection portion rotate/rotates relative to the treatment bed so that a distance of the probing device in the first detection portion relative to the treatment bed and a distance of the probing device in the second detection portion relative to the treatment bed are equal to each other.

More particularly, the photon emission detection device is connected to a signal acquisition unit configured to collect the gamma rays detected by the detection portion and a calculation unit configured to calculate a boron concentration according to the acquired signals.

More particularly, the photon emission detection device is further connected to a feedback unit coupled to the neutron capture therapy device, and the feedback unit generates a feedback signal of a concentration of the calculated boron ($^{10}$B) to the neutron capture therapy device in real time.

Further, the neutron capture therapy device is coupled with a correction unit configured to correct the irradiation time of the neutron capture therapy device to tumor based on the feedback signal of the feedback unit.

Further, the beam shaping assembly includes a moderator configured to moderate the neutrons generated from the neutron generator to a preset energy spectrum and a reflector surrounding the moderator and configured to direct the deviated neutrons back to increase the neutron intensity within the preset energy spectrum.

In order to improve the detecting accuracy of the photon emission detection device, yet another aspect of the present disclosure provides a photon emission detection device, the photon emission detection device is used in a boron neutron capture therapy system comprising a treatment bed and a neutron capture therapy device, wherein the neutron capture therapy device comprises an accelerator configured to generate a charged particle beam; a neutron generator configured to generate a neutron beam after being irradiated by the charged particle beam; a beam shaping assembly configured to shape the neutron beam; and a collimator configured to converge the neutrons generated by the neutron generator; wherein the photon emission detection device forms a ring whose radius is configured to be increased or decreased, and the ring surrounds the treatment bed, wherein the photon emission detection device comprises means for providing a concentration of boron from gamma rays generated after irradiating a boron-containing drug with neutrons.

Further, the photon emission detection device is connected to a signal acquisition unit configured to collect the gamma rays detected by the detection portion and a calculation unit configured to calculate a boron concentration of the target according to the acquired signals by the signal acquisition unit.

Further, the photon emission detection device is connected to a feedback unit coupled to the neutron capture therapy device, and the feedback unit generates a feedback signal of the concentration of the calculated boron ($^{10}$B) to the neutron capture therapy device in real time.

Further, the neutron capture therapy device is coupled with a correction unit configured to correct the irradiation time of the neutron capture therapy device to the target based on the feedback signal of the feedback unit.

Compared to the prior art, the photon emission detection device can adjust the radius of the ring around the treatment bed according to the actual situation of the detected object so as to improve the detecting accuracy of the photon emission detection device.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure.

Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

As used herein, the term "unit" may refer to a computer module implemented by hardware and/or software components, and the computer module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

Figure 1:
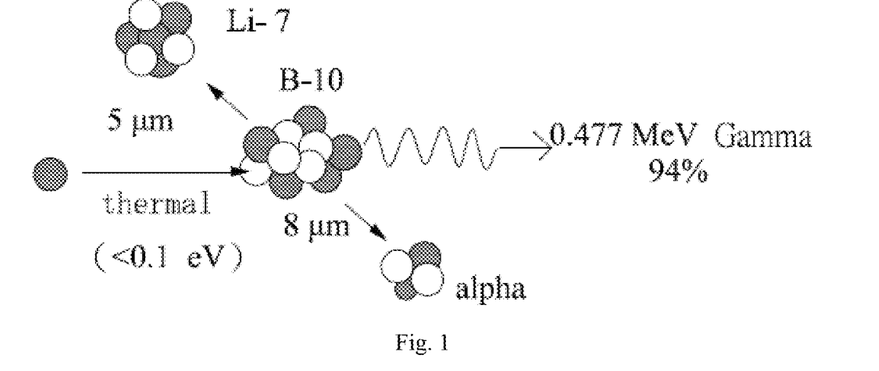
FIG. 1 is a schematic view of boron neutron capture reaction.
Figure 2:
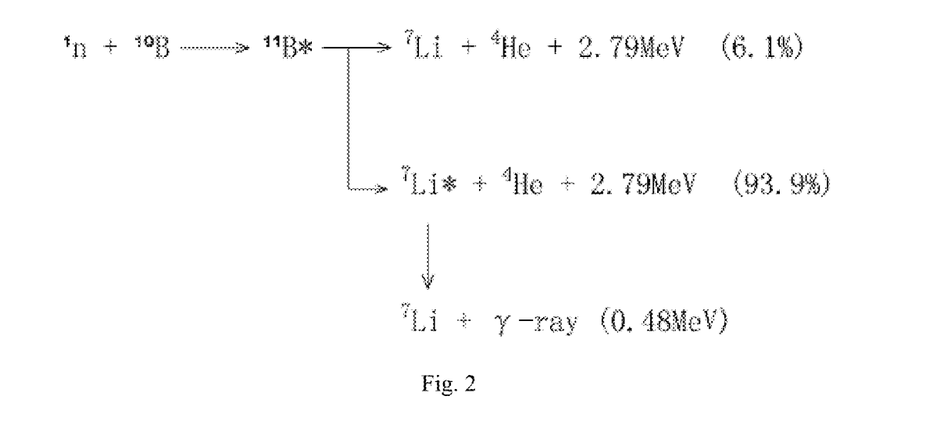
FIG. 2 is a nuclear reaction formula of $^{10}B(n,\alpha)^7Li$ neutron capture.

Neutron capture therapy (NCT) has been increasingly practiced as an effective cancer curing means in recent years, and BNCT is the most common. Neutrons for NCT may be supplied by nuclear reactors or accelerators. BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. As illustrated in FIG. 1, a schematic view of boron neutron capture reaction are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7Li$ are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

The present application discloses a photon emission detection device used for a boron neutron capture therapy system for detecting gamma rays generated after a neutron beam generated by the neutron capture therapy device reacts with a boron ($^{10}B$)-containing drug, thereby calculating a concentration of boron ($^{10}B$) by the gamma ray.

The photon emission detection device applied to the boron neutron capture therapy system will be specifically described below with reference to the accompanying drawings.

Figure 3:
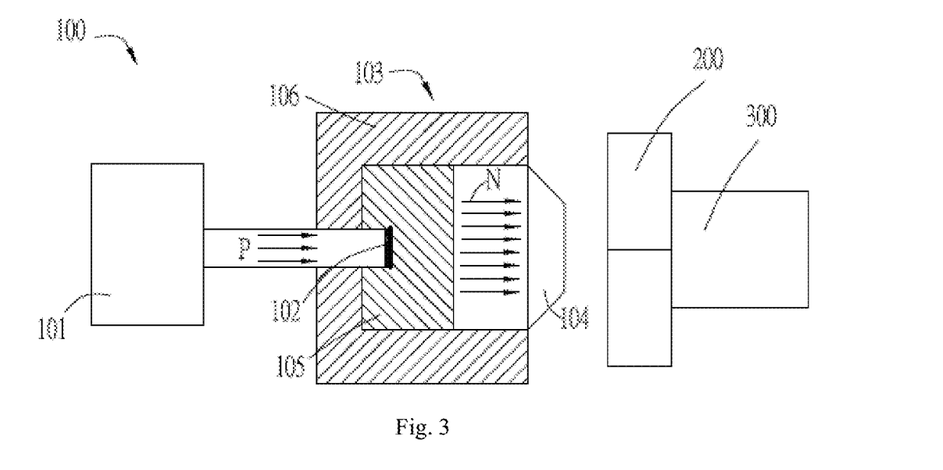
FIG. 3 is a schematic view of a neutron capture therapy device of the present disclosure.

As shown in FIG. 3, the boron neutron capture therapy system comprises a neutron capture therapy device 100, a photon emission detection device 200, and a treatment bed 300. The neutron capture therapy device 100 comprises an accelerator 101 for generating a charged particle beam, a neutron generator 102 for generating a neutron beam N after being irradiated by the charged particle beam P, a beam shaping assembly 103 for shaping the neutron beam N and a collimator 104. The beam shaping assembly 103 comprises a moderator 105 and a reflector 106 surrounding the moderator 105. The moderator 105 decelerates the neutrons generated from the neutron generator 102 to a preset energy spectrum. The reflector 106 directs the deviated neutrons back to increase the neutron intensity within the preset energy spectrum, and the collimator 104 converges the neutrons generated by the neutron generator 102.

After the patient is administrated or injected with a boron ($^{10}B$)-containing drug, the boron ($^{10}B$)-containing drug selectively accumulates in the tumor cells. Gamma rays are generated after the boron ($^{10}B$)-containing drug is irradiated by the neutrons, and the gamma rays are detected by the photon emission detection device.

Figures 4, 5:
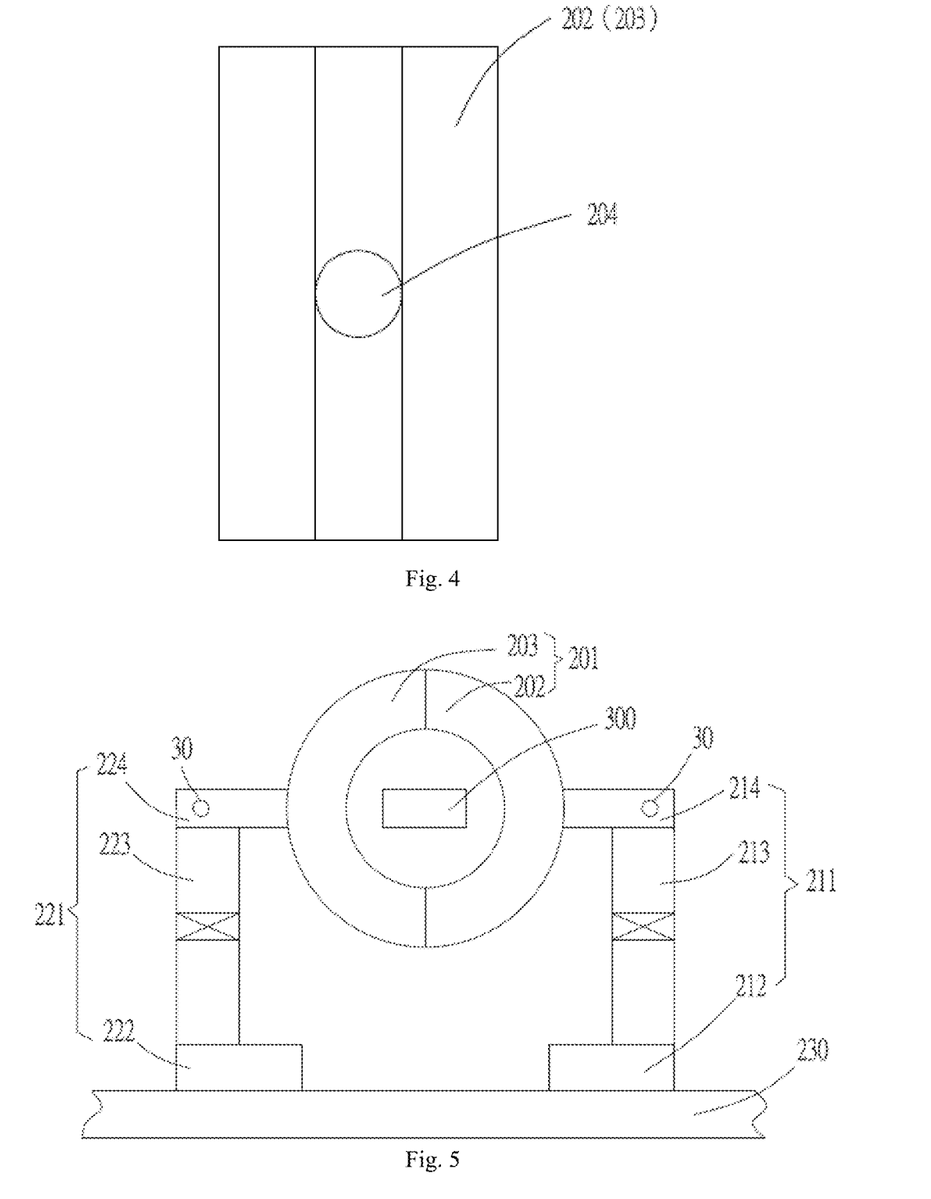
FIG. 4 is a schematic view showing a state in which the detecting portion of the photon emission detection device of the present disclosure surrounds the treatment bed with a maximum radius.
FIG. 5 is a schematic view of another angle of the detecting portion of the photon emission detection device of the present disclosure.
Figure 6:
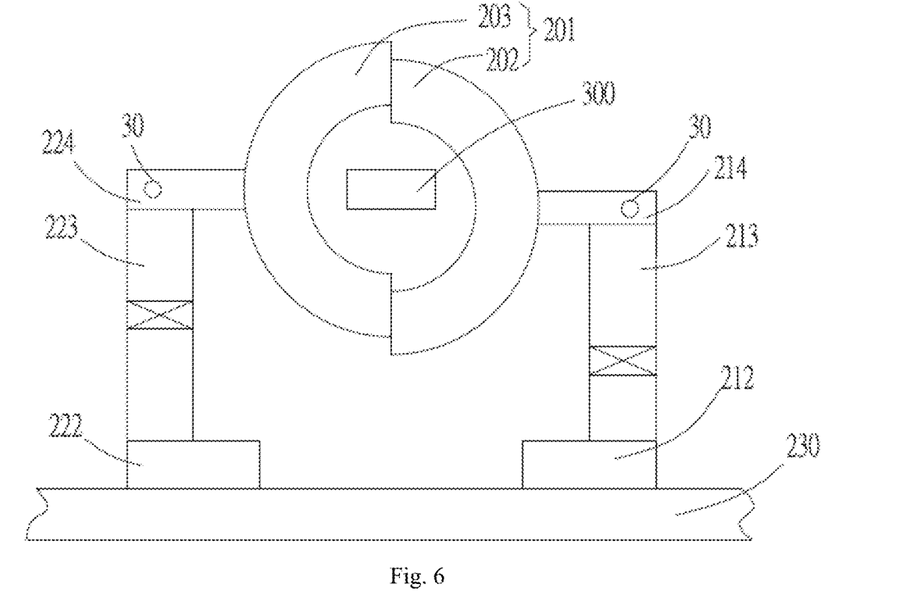
FIG. 6 is a schematic view showing a state in which the detecting portion of the photon emission detection device of the present disclosure surrounds the treatment bed with a reduced radius.

As shown in FIGS. 4 to 6, the photon emission detection device 200 comprises a detecting portion 201 surrounding the treatment bed, the detecting portion 201 comprises a first detecting portion 202 and a second detecting portion 203, the first detecting portion 202 and the second detecting portion 203 move away from or close to each other so as to form a ring of the detecting portion surrounding the treatment bed 300, and the radius of the ring can be increased or decreased. Each of the first detecting portion 202 and the second detecting portion 203 is mounted with a probing device 204 that can be distributed in the first detecting portion 202 and the second detecting portion 203 to rotate 180 degrees with respect to the treatment bed, and the detecting portion 201 realizes the detection of the gamma rays by the probing device 204.

As an embodiment, in the present application, the first detecting portion 202 and the second detecting portion 203 move away from or close to each other by the following means.

The photon emission detection device 200 further comprises a first supporting frame 211 and a second supporting frame 221 located on two sides of the treatment bed 300. The first supporting frame 211 comprises a first pedestal 212 capable of moving on the ground, a first telescopic arm 213 connected to the first pedestal 212, and a first extending arm 214 located at one end of the first telescopic arm 213 and connected to the first detecting portion 202. The first telescopic arm 213 extends and retracts in a vertical direction. The first detecting portion 202 is disposed at the first extending arm 214, the first detecting portion 202 and the first extending arm 214 move up and down in accordance with the extending or retracting movement of the first telescopic arm 213. The second supporting frame 221 comprises a second pedestal 222 capable of moving on the ground, a second telescopic arm 223 connected to the second pedestal 222, and a second extending arm 224 located at one end of the second telescopic arm 223 and connected to the second detecting portion 203. The second telescopic arm 223 extends and retracts in the vertical direction, the second detecting portion 203 is disposed at the second extending arm 224, the second detecting portion 203 and the second extending arm 224 move up and down in accordance with the extending and retracting movement of the second telescopic arm 223. The first supporting frame 211 and the second supporting frame 221 moves away from or close to the treatment bed 300 as the first pedestal 212 and the second pedestal 222 move. For the convenience of manufacture, as an embodiment, the first supporting frame 211 and the second supporting frame 221 have the same structure. In addition, the first telescopic arm 213 and the second telescopic arm 223 may be configured as a non-retractable structure, the first extending arm 214 and the second extending arm 224 are configured to be rotatable relative to the first telescopic arm 213 and the second telescopic arm 223, respectively. The radius of the detecting portion 201 surrounding the treatment bed 300 is changed by rotating the first and second extending arms 213, 223. Certainly, the rotating structure of the first extending arm 214 and the second extending arm 224 and the telescopic structure of the first telescopic arm 213 and the second telescopic arm 223 can be simultaneously adopted to increase the degree of freedom of the detecting portion 201.

As an embodiment, a first rotating member 30 is disposed between the first telescopic arm 213 and the first extending arm 214 in the present disclosure. That is, the first extending arm 214 is rotatable relative to the first telescopic arm 213 about the first rotating member 30. A second rotating member 30 is also disposed between the second telescopic arm 223 and the second extending arm 224, the second extending arm 224 is rotatable relative to the second telescopic arm 223 about the second rotating member 30. The advantage is that the radius of the detecting portion 201 surrounding the treatment bed 300 can be changed by rotating the first and second extending arms 213, 223, at the same time, the degree of freedom of the entire probing device 204 can be further increased, and it is easier to adjust the distances of the first detecting portion 201 and the second detecting portion 202 to the tumor position. That is, it can be advantageous to adjust the distance of the first detecting portion 201 to the tumor position to be equal to the distance of the second detecting portion 202 to the tumor position, so as to improve the detecting accuracy of the entire probing device 204.

In the actual detecting process, the tumor location of different patients is likely to be different. For example, some patients have tumors in the head, some patients have tumors in the chest. If the tumor site to be detected in the patient on the treatment bed is in the head, the ring radius of the first detecting portion 202 and the second detecting portion 203 surrounding the treatment bed 300 is preferably small, and if the tumor site to be detected is the chest, then the radius of the ring formed by the first detecting portion and the second detecting portion surrounding the treatment bed is changed according to actual measurement requirements. Because the smaller the ring radius of the detecting portion surrounding the treatment bed is, the closer the probing device 204 installed in the detecting portion 201 is to the patient, and the detection distance of the probing device 204 relative to the tumor site of the patient is reduced, the detected related information becomes more, and the detecting accuracy of the entire photon emission detection device 200 will be higher.

When it is necessary to reduce the ring radius surrounding the treatment bed 300, change the telescopic length of the first telescopic arm 213 or the second telescopic arm 223 so as to keep the telescopic lengths of the first telescopic arm 213 and the second telescopic arm 223 different, and transfer the first pedestal 212 and the second pedestal 222 so as to bring the first pedestal 212 and the second pedestal 222 closer to each other, so that the radius of the first detecting portion 202 and the second detecting portion 203 surrounding the patient's tumor is reduced (the distance from the detection device 204 to the tumor location is reduced). When it is desired to increase the radius of ring surrounding the treatment bed 300, keep the telescopic distances of the first telescopic arm 213 and the second telescopic arm 223 the same, and transfer the first pedestal 212 and the second pedestal 222 to move away from each other, so that the radius of the first detecting portion 202 and the second detecting portion 203 surrounding the patient's chest is increased. When telescopic distance of the first telescopic arm 213 and the second telescopic arm 223 are the same, the first pedestal 211 and the second pedestal 221 are moved close to each other until the first detecting portion 202 and the second detecting portion 203 contact with each other, the first detecting portion 202 and the second detecting portion 203 form a ring having the maximum radius surrounding the treatment bed 300.

The movement of the first pedestal 212 and the second pedestal 222 can be achieved by arranging tracks 230 on the ground. Specifically, arrange a track 230 on the ground at each side of the treatment bed 300, the first and second pedestals 212, 222 are respectively mounted on the track 230 and capable of moving on the track 230. The movement of the first and second pedestals 212, 222 drives the first and second detecting portions 202, 203 to move close to or away from each other, so that the radius of the first detecting portion 202 and the second detecting portion 203 surrounding the treatment bed 300 is increased or decreased.

In the present embodiment, the treatment bed 300 can move back and forth in the ring formed by the first detecting portion 202 and the second detecting portion 203 to change the relative position between the probing device 204 and the treatment bed 300 (i.e., to change the relative position between the probing device 204 and the tumor). Since the treatment bed 300 can move back and forth, it is only necessary to arrange the track 230 to be a structure located on both sides of the treatment bed 300 and capable of moving in a direction perpendicular to the direction of movement of the treatment bed 300. The first and second pedestals 211, 221 are mounted on the track 230 and move along the track 230 to move away from or close to the treatment bed 300.

Because the radius of the detecting portion 201 surrounding the treatment bed 300 can be changed according to the actual size of the patient's tumor position during the actual treatment, and the treatment bed 300 can also be moved according to the actual situation of the patient's tumor position, so as to make the patient's tumor site between the detecting portions 201 and realize omnidirectional detection of the patient's tumor by using the entire photon emission detection device 200 coupled with the treating bed 300.

When the boron neutron capture therapy is completed, transfer the first pedestal 211 and the second pedestal 221 to divide the entire photon emission detection device 200 into two parts and move the two parts away from the treatment bed 300.

Figure 7:
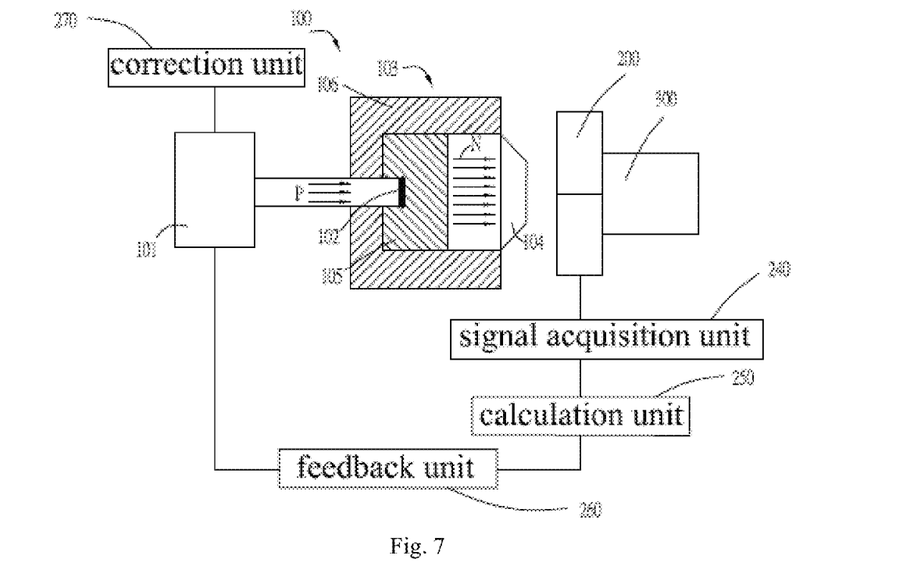
FIG. 7 is a schematic block diagram of a photon emission detection device and a neutron capture therapy device of the present disclosure.

Referring to FIG. 7, the photon emission detection device 200 is further connected to a signal acquisition unit 240 that collects the gamma rays detected by the detecting portion 201, a calculation unit 250 that calculates the concentration of boron through the acquired signals, and a feedback unit 260 coupled to the neutron capture therapy device 100, the feedback unit 260 generates a feedback signal of the calculated concentration of boron to the neutron capture therapy device 100 in real time, the neutron capture therapy device 100 is coupled with a correction unit 270 capable of correcting the irradiation time of the neutron beam generated by the neutron capture therapy device 100 to the tumor based on the feedback signal by the feedback unit 260.

The operating process of the photon emission detection device in the entire boron neutron capture therapy system is now described as below.

First, the patient is injected (administered) with a boron ($^{10}$B) drug and placed on the treatment bed 300, and the boron ($^{10}$B)-containing drug is accumulated at the patient's tumor site;

The photon emission detection device 200 sequentially adjusts the position of the treatment bed 300 relative to the detecting portion 201 according to the portion of the patient's tumor (the tumor site is located in the corresponding position of the probing device 204 in the detecting portion 201 by the movement of the treatment bed 300) and the ring radius of the first detecting portion 202 and the second detecting portion 203 surrounding the treatment bed 300;

The neutron capture therapy device 100 generates a neutron beam N irradiates to a tumor site of the patient in which boron ($^{10}$B)-containing drug is accumulated, and gamma rays are generated by the reaction of neutron beam N and boron ($^{10}$B);

The gamma rays generated by the reaction of the neutron beam N and boron ($^{10}$B) is detected by the first detecting portion 202 and the second detecting portion 203 through the probing device 204;

The signal acquisition unit 240 collects the detected gamma rays and calculates the concentration of boron ($^{10}$B) from the acquired gamma rays by using the calculation unit 250;

The feedback unit 260 generates a feedback signal of the calculated concentration of boron ($^{10}$B) to the neutron capture therapy device 100;

The neutron capture therapy device 100 corrects the irradiation time of the neutron beam according to the concentration of boron ($^{10}$B) feedback signal by the feedback unit 260 through the correction unit 270.

When the entire treatment process is over, the photon emission detection device 200 can be divided into two parts and the two parts move to a position away from the neutron capture treatment device 100 to reduce the radiation influence between the neutron capture therapy device 100 and the photon emission detection device 200.

The photon emission detection device for the boron neutron capture therapy system disclosed in the present disclosure is not limited to the contents described in the above embodiments and the structures represented by the drawings. If necessary, the improvement in the present disclosure can be performed on other tomographic imaging devices (such as Computed Tomography: CT). Modifications, substitutions, or alterations to the materials, shapes, and positions of the components in the present disclosure are within the scope of the present disclosure.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A photon emission detection device, comprising:
   a treatment bed;
   a detecting portion including a first detecting portion and a second detecting portion on two sides of the treatment bed respectively; and
   a first supporting frame and a second supporting frame respectively disposed on the two sides of the treatment bed;
   wherein the first detecting portion and the second detecting portion move away from or close to each other so that the detecting portion forms a ring whose radius is configured to be increased or decreased, and the ring surrounds the treatment bed.

2. The photon emission detection device according to claim 1, wherein each of the first detecting portion and the second detecting portion is mounted with a corresponding probing device configured to rotate relative to the treatment bed, and each of the first detecting portion and the second detecting portion detects gamma rays generated by a boron neutron capture reaction through the corresponding probing device.

3. The photon emission detection device according to claim 1,
   wherein the first supporting frame comprises a first pedestal configured to move on a ground, a first telescopic arm connected to the first pedestal and configured to stretch and retract in a vertical direction, and a first extending arm located at one end of the first telescopic arm and connected to the first detecting portion, and the first detecting portion is disposed at the first extending arm;
   wherein the second supporting frame comprises a second pedestal configured to move on the ground, a second telescopic arm connected to the second pedestal and configured to stretch and retract in the vertical direction, and a second extending arm located at one end of the second telescopic arm and connected to the second detecting portion, the second detecting portion is disposed at the second extending arm; and
   wherein the first supporting frame moves away from or close to the treatment bed in response to moving of the first pedestal, and the second supporting frame moves away from or close to the treatment bed in response to moving of the second pedestal.

4. The photon emission detection device according to claim 3, wherein when the first telescopic arm and the second telescopic arm have a same telescopic distance, and the first pedestal and the second pedestal move towards each other until the first detecting portion and the second detecting portion are in contact with each other, the first detecting portion and the second detecting portion form a maximum ring having a maximum radius surrounding the treatment bed; and when the first telescopic arm and the second telescopic arm have different telescopic distances, and the first pedestal and the second pedestal move towards each other, the first detecting portion and the second detecting portion form a reduced ring having a reduced radius surrounding the treatment bed.

5. The photon emission detection device according to claim 3, wherein a first rotating member is disposed between the first telescopic arm and the first extending arm, and a second rotating member is provided between the second telescopic arm and the second extending arm, the first extending arm rotates about the first rotating member so that the first detecting portion rotates relative to the treatment bed, and the second extending arm rotates about the second rotating member so that the second detecting portion rotates relative to the treatment bed.

6. The photon emission detection device according to claim 3, wherein a track is arranged on the ground at each of the two sides of the treatment bed, and the first pedestal and the second pedestal are respectively mounted on the track.

7. The photon emission detection device according to claim 1, wherein at least one of the first detecting portion and the second detecting portion rotates relative to the treatment bed.

8. The photon emission detection device according to claim 1, wherein the treatment bed moves back and forth in the ring formed by the detecting portion.

9. A photon emission detection device used in a boron neutron capture therapy system comprising a treatment bed and a neutron capture therapy device, wherein the neutron capture therapy device comprises:
an accelerator configured to generate a charged particle beam;
a neutron generator configured to generate a neutron beam after being irradiated by the charged particle beam;
a beam shaping assembly configured to shape the neutron beam; and
a collimator configured to converge neutrons generated by the neutron generator;
wherein the photon emission detection device comprises a detecting portion surrounding the treatment bed and configured to detect gamma rays generated after irradiating a boron ($^{10}$B)-containing drug with neutrons, the detecting portion forms a ring whose radius is configured to be increased or decreased, and the ring surrounds the treatment bed.

10. The photon emission detection device according to claim 9, wherein the detecting portion comprises a first detecting portion and a second detecting portion respectively disposed on each side of the treatment bed, the first detecting portion and the second detecting portion move away from or close to each other so that the ring radius of the detecting portion is configured to be increased or decreased.

11. The photon emission detection device according to claim 10, wherein each of the first detecting portion and the second detecting portion is mounted with a corresponding probing device configured to rotate relative to the treatment bed, and each of the first detecting portion and the second detecting portion detects the gamma rays by the corresponding probing device.

12. The photon emission detection device according to claim 11, wherein at least one of the first detecting portion and the second detecting portion rotates relative to the treatment bed so that a distance of the corresponding probing device in the first detecting portion relative to the treatment bed and a distance of the corresponding probing device in the second detecting portion relative to the treatment bed are equal to each other.

13. The photon emission detection device according to claim 9, wherein the photon emission detection device is connected to a signal acquisition unit configured to collect and acquire signals corresponding to the gamma rays detected by the detecting portion and a calculation unit configured to calculate a boron concentration according to the signals acquired by the signal acquisition unit.

14. The photon emission detection device according to claim 13, wherein the photon emission detection device is further connected to a feedback unit coupled to the neutron capture therapy device, and the feedback unit generates a feedback signal of the boron concentration calculated by the calculation unit to the neutron capture therapy device in real time.

15. The photon emission detection device according to claim 14, wherein the neutron capture therapy device is coupled with a correction unit configured to correct irradiation time of the neutron capture therapy device to tumor based on the feedback signal of the feedback unit.

16. The photon emission detection device according to claim 9, wherein the beam shaping assembly comprises a moderator configured to moderate the neutrons generated from the neutron generator to a preset energy spectrum and a reflector surrounding the moderator and configured to direct deviated neutrons back to increase a neutron intensity within the preset energy spectrum.

17. A photon emission detection device used in a boron neutron capture therapy system comprising a treatment bed and a neutron capture therapy device, wherein the neutron capture therapy device comprises,
an accelerator configured to generate a charged particle beam;
a neutron generator configured to generate a neutron beam after being irradiated by the charged particle beam;
a beam shaping assembly configured to shape the neutron beam; and
a collimator configured to converge neutrons generated by the neutron generator;
wherein the photon emission detection device forms a ring whose radius is configured to be increased or decreased, and the ring surrounds the treatment bed,
wherein the photon emission detection device comprises means for providing a concentration of boron from gamma rays generated after irradiating a boron-containing drug with neutrons.

18. The photon emission detection device according to claim 17, wherein the photon emission detection device is connected to a signal acquisition unit configured to collect and acquire signals corresponding to the gamma rays detected by a detecting portion and a calculation unit configured to calculate a boron concentration of a target according to the signals acquired by the signal acquisition unit.

19. The photon emission detection device according to claim 18, wherein the photon emission detection device is connected to a feedback unit coupled to the neutron capture therapy device, and the feedback unit generates a feedback signal of the boron concentration calculated by the calculation unit to the neutron capture therapy device in real time.

20. The photon emission detection device according to claim 19, wherein the neutron capture therapy device is coupled with a correction unit configured to correct irradiation time of the neutron capture therapy device to the target based on the feedback signal of the feedback unit.

* * * * *